(12) United States Patent
Strauss

(10) Patent No.: US 8,328,817 B2
(45) Date of Patent: Dec. 11, 2012

(54) MULTIPLANAR TAPER LOCK SCREW AND LOCK INDICATOR GAUGE

(75) Inventor: Kevin R. Strauss, Leesburg, VA (US)

(73) Assignee: K2M, Inc., Leesburg, VA (US)

( * ) Notice: Subject to any disclaimer, the term of this patent is extended or adjusted under 35 U.S.C. 154(b) by 477 days.

(21) Appl. No.: 12/612,960

(22) Filed: Nov. 5, 2009

(65) Prior Publication Data

US 2010/0114108 A1     May 6, 2010

Related U.S. Application Data

(60) Provisional application No. 61/198,393, filed on Nov. 5, 2008.

(51) Int. Cl.
*A61B 17/58* (2006.01)
*A61B 17/60* (2006.01)
*A61F 2/00* (2006.01)

(52) U.S. Cl. ......... 606/102; 606/266; 606/308; 606/104

(58) Field of Classification Search ................. 606/264, 606/265, 305, 307, 102
See application file for complete search history.

(56) References Cited

U.S. PATENT DOCUMENTS

| | | | |
|---|---|---|---|
| 2005/0222575 A1* | 10/2005 | Ciccone et al. | 606/104 |
| 2007/0167954 A1* | 7/2007 | Sicvol et al. | 606/104 |

* cited by examiner

*Primary Examiner* — Andrew Yang
(74) *Attorney, Agent, or Firm* — Carter, DeLuca, Farrell & Schmidt, LLP

(57) ABSTRACT

A lock indicator gauge is provided to provide an indication as to whether a bone screw construct is in a locked or an unlocked condition when the lock indicator gauge is operatively engaged with the bone screw construct. A plunger longitudinally disposed within a housing of the lock indicator gauge translates within the housing by a distance that corresponds to the relative positions of inner and outer housings of the bone screw construct, wherein the relative positions of the inner and outer housings is dependent on whether the bone screw construct is in a locked or an unlocked condition.

12 Claims, 7 Drawing Sheets

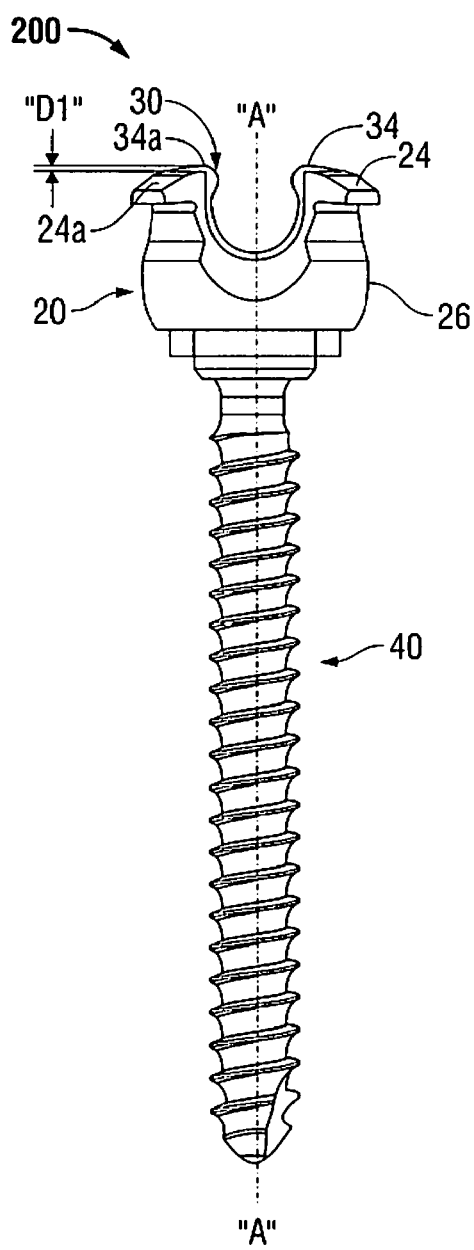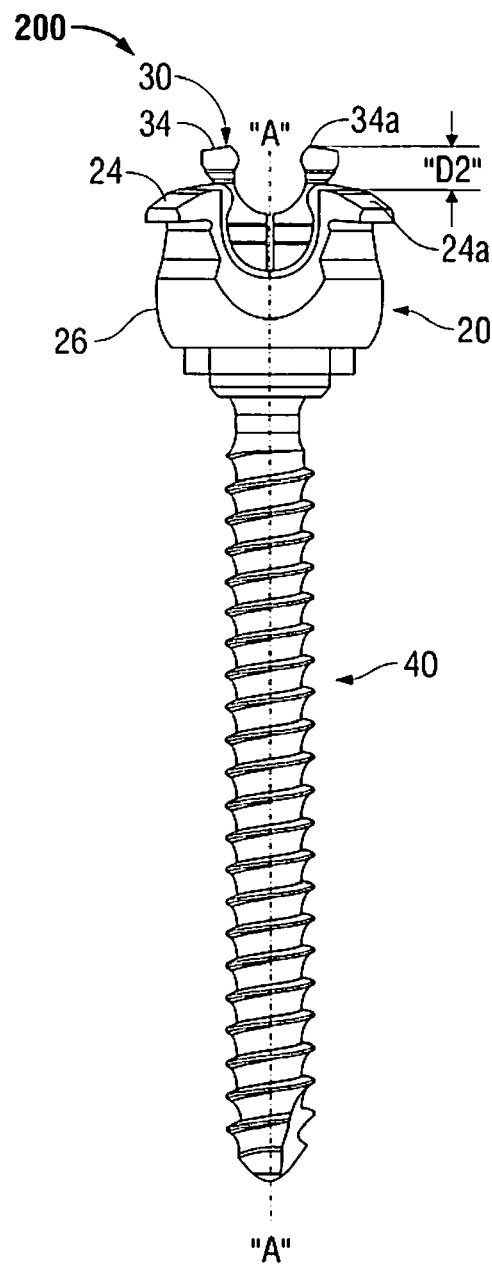
FIG. 1A
FIG. 1B

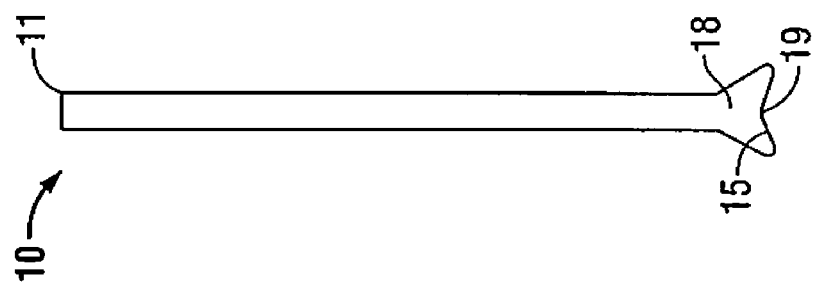
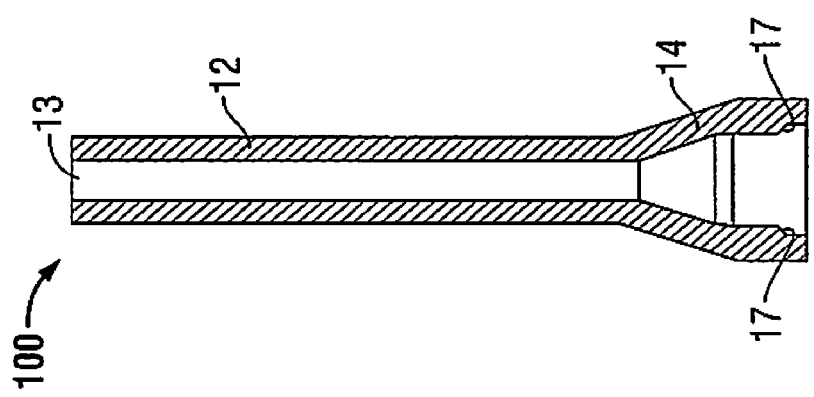
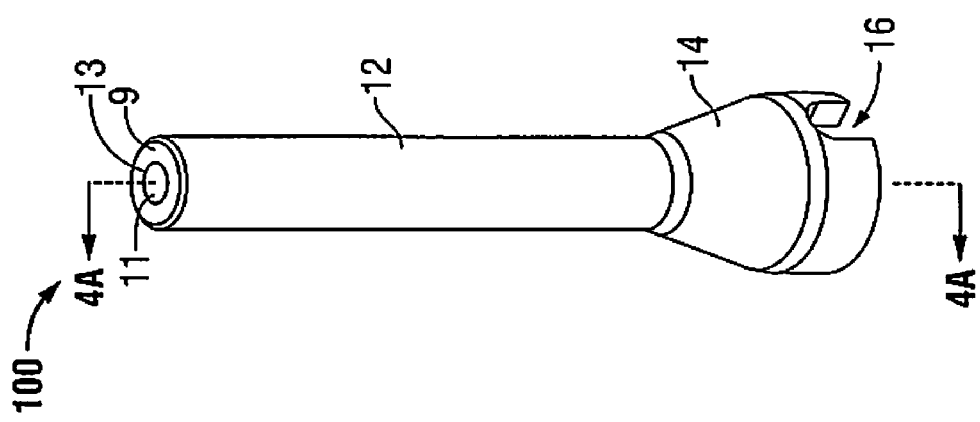

MULTIPLANAR TAPER LOCK SCREW AND LOCK INDICATOR GAUGE

CROSS REFERENCE TO RELATED APPLICATIONS

This application claims priority to, and benefit of, U.S. Provisional Patent Application Ser. No. 61/198,393, filed Nov. 5, 2008. The disclosure of this application is hereby incorporated by reference in its entirety.

BACKGROUND

1. Technical Field

The present disclosure relates to gauges that indicate the state or condition of a bone fixation device, e.g., whether the bone fixation device is locked or unlocked. More particularly the present disclosure relates to a lock indicator gauge to indicate whether a bone screw, e.g., a multiplanar taper lock screw for securing a spinal rod to a vertebra, is in a locked or in an unlocked state.

2. Background of Related Art

Correction of a spinal deformity typically requires stabilization and fixation of vertebrae in a particular spatial relationship. Surgical spinal correction procedures involve the placement of a plurality of bone pins, anchors, cables, hooks, or screws placed in adjacent vertebrae and using spinal rods to maintain a predetermined spatial relationship between the vertebrae.

These devices commonly employ longitudinal link rods secured to vertebrae by spinal bone fixation fasteners, such as pedicle screws and hooks. Conventional devices for locking a spinal rod to a fixation hook or screw do not offer the needed variability to allow the spinal rod to be easily connected to adjacent vertebrae that are not aligned on the same plane.

In some cases, such devices are permanently implanted in the subject. However, in other cases, the devices may be subsequently removed when no longer needed. Moreover, it is common that devices that were intended to be permanently implanted may require subsequent procedures or revisions as the patient's condition necessitates. For this reason, it is desirable that an implanted device be readily locked and unlocked as desired by a surgeon. Determination of whether an implanted device is locked or unlocked may not be readily apparent by merely visually inspecting the device.

SUMMARY

Disclosed herein is a lock indicator gauge adapted and configured to provide an indication of whether a bone screw construct is in a locked or an unlocked position. In an embodiment, the lock indicator gauge is adapted and configured to provide an indication of the relative position of an inner and an outer housing of the bone screw construct. Since the relative position of the inner and outer housings in the locked and unlocked states or conditions is known, an indication of the relative position of the inner and outer housings provides for determination of the state of the bone screw construct.

In an embodiment, the lock indicator gauge includes a housing that includes a proximal end, a distal end, and a first longitudinal axis. A plunger is longitudinally disposed within the housing, along the first longitudinal axis. The distal end of the housing is adapted to receive a proximal end of a bone screw construct having an inner housing, e.g., collet, and an outer housing, e.g., coupling. The inner and outer housing share a common second longitudinal axis that is coaxial with the first longitudinal axis when the lock indicator gauge engages the proximal end of the bone screw construct. Each of the inner and outer housings has a position along the second longitudinal axis that may be equal or different. Placement of the lock indicator gauge atop the bone screw construct results in displacement or translation of the plunger proximally through the housing by a distance corresponding to the difference in position of the outer and inner housings of the bone screw construct along the second longitudinal axis. An indicator provides indication of the position of the plunger relative to the housing.

In an embodiment, the distal end of the plunger functions as an indicator by extending through a lumen at the proximal end of the housing by a distance corresponding to the distance defined by the relative positions of the inner and outer housings of the bone screw construct. The plunger may include at least one visual cue along a longitudinal surface of the plunger, i.e., the shaft of the plunger. The at least one visual cue may be, but is not limited to, a mark, a groove, a color, or a word.

In embodiments, the lock indicator gauge may provide a visual, tactile, and/or audible indication of the position of the plunger relative to the housing of the lock indicator gauge.

The various embodiments of the present disclosure will be more readily understood from the following detailed description when read in conjunction with the appended figures.

BRIEF DESCRIPTION OF THE DRAWINGS

Embodiments of the present disclosure are described herein with reference to the accompanying drawings, wherein:

FIG. 1A is a front view of a bone screw construct shown in a first condition;

FIG. 1B is a front view of the bone screw construct of FIG. 1A shown in a second condition;

FIG. 4 is an isometric view of a lock indicator gauge including a housing and a plunger;

FIG. 4A is a cross-sectional view of the housing of FIG. 4 taken along section line 4A-4A;

FIG. 4B is a front view of the plunger of FIG. 4;

DETAILED DESCRIPTION

Figure 2:
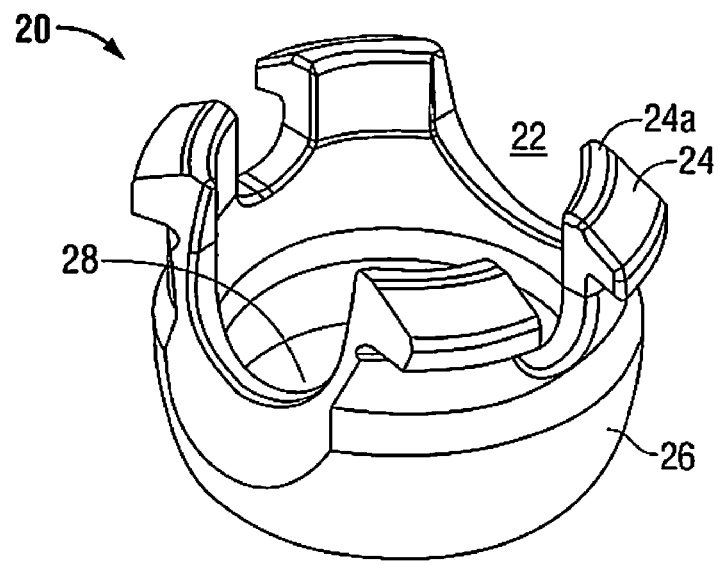
FIG. 2 is a top perspective view of an outer housing or coupling.

Embodiments of the present disclosure will now be described in detail with reference to the drawings, wherein the reference numerals identify similar or identical elements. In the drawings and in the description that follows, the term "proximal," will refer to the end of a gauge or system that is closest to the operator, while the term "distal" will refer to end of the gauge or system that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure coupled hereto.

A bone screw construct 200 will now be described with reference to FIGS. 1A-3. The bone screw construct 200 includes an outer housing or coupling 20 (FIG. 2), an inner housing or collet 30 (FIG. 3), and a bone screw 40. The bone screw 40 is a multi-planar taper lock screw and includes a screwhead 42 (FIG. 7A) that is rotatable and pivotable relative to coupling 20 and collet 30, thereby allowing the screw 40 to be positioned in a plurality of orientations relative to the coupling 20 and the collet 30. The bone screw construct 200 is operatively connectable to a rod (not shown). The ability to position the bone screw 40 in a plurality of orientations relative to the coupling 20 and the collet 30 facilitates the operative coupling of the rod to vertebrae that are not coplanar or other bone structures that have a discontinuity.

As shown in FIG. 2, the coupling 20 includes an annular body portion 26 including an opening 28 that extends axially therethrough. Additionally, the coupling 20 includes a plurality of fingers 24 that are located in opposing regions of the coupling 20 and define a saddle 22 having a generally U-shaped configuration. The U-shaped saddle 22 is configured and dimensioned for receiving the rod.

Figure 3:
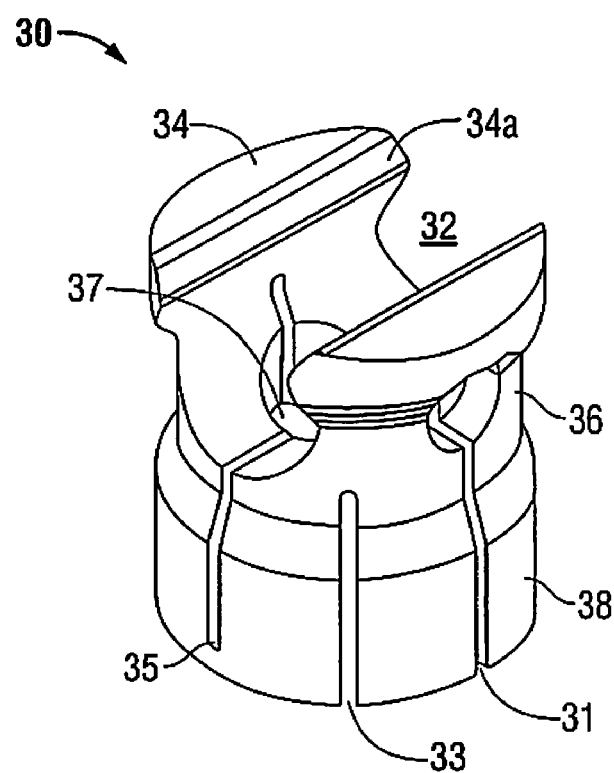
FIG. 3 is a top perspective view of an inner housing or collet.

The collet 30, shown in FIG. 3, is configured and adapted to be placed within coupling 20. Collet 30 has a generally cylindrical body portion 36 including an opening 37 extending axially therethrough. A pair of upstanding wings 34 defines a saddle 32 having a generally U-shaped configuration. The saddle 32 is configured and dimensioned for receiving a rod (not shown). The body portion 36 includes a slot 35 that extends from the nadir of the saddle 32 towards the bottom of the body portion 36 and essentially bisects the body portion 36 along a central axis, and defines left and right sections of the body portion. Preferably, the slot 35 does not extend all the way through the body portion. Although less desirable, such a full slot could be used. In addition to slots 35, a plurality of grooves 31 and notches 33 may facilitate flexure of the collet 30 in response to compressive and tensile forces. This arrangement permits each of the wings 34 to flex towards and away from each other. The dimensions of the saddle 32 vary according to the flexure of the wings 34. As the wings 34 are moved closer to each other, the saddle 32 decreases in size and when the wings 34 are moved away from each other, the saddle 32 increases in size. Allowing the saddle 32 to vary in size permits the collet 30 to accommodate rods having different outside diameters. Compression of the wings 34 towards each other increasingly engages the outer surface of the rod when the rod is located in the saddle 32, thereby frictionally securing the rod in a desired position.

Collet 30 is retained within the coupling 20. Collet 30 and coupling 20 are slidable relative to one another, as seen in FIGS. 1A and 1B. When the bone screw construct 200 is in a locked position, as shown in FIG. 1A, the collet 30 is substantially within coupling 20, the collet 30 is compressed such that the dimensions of saddle 32 are sized to frictionally secure a rod placed within saddle 32. While in the locked position, the relative position between a proximal surface 24a of finger 24 of the coupling 20 and a proximal surface 34a of wing 34 of the collet 30 along an axis "A" is equal to a distance "D1". Conversely, when in the unlocked position, the relative position between a proximal surface 24a of finger 24 of the coupling 20 and a proximal surface 34a of wing 34 of the collet 30 along an axis "A" is equal to a distance "D2". Distance "D2" is greater than distance "D1" and indicates that the collet 30 is not substantially positioned within the coupling 20. When the collet 30 is not substantially positioned within the coupling 20, the collet 30 is not sufficiently compressed to secure rod when placed within saddle 32, and the bone screw construct is in the unlocked position.

A lock indicator gauge 100, described with reference to FIGS. 4-8A, is configured and adapted to interact with the bone screw construct 200 to provide an indication of whether the bone screw construct 200 is in a locked or in an unlocked state or condition. The lock indicator gauge 100 may provide a visual, tactile, and/or audible indication of the condition of the bone screw construct 200. While the function of the lock indicator gauge 100 will be described herein with reference to the bone screw construct 200, it is to be understood that the lock indicator gauge 100 may be used with a variety of bone screw constructs. Examples of some suitable bone screw constructs are found in International Patent Application PCT/US08/80682, the entire contents of which are incorporated by reference.

As shown in FIG. 4, the lock indicator gauge 100 includes a housing 12, a receptacle 14, and an indicator button 11 disposed a proximal end of a plunger 10 that is longitudinally disposed within housing 12 (FIG. 4B). As seen in FIG. 4A, the housing includes a through hole or lumen 13 that extends the length of the housing 12 and a receptacle 14 that is adapted and configured to receive a proximal end of the bone screw construct 200 therein. The receptacle 14 includes contacting members 17 that are configured and adapted to position the housing 12 coaxially with a longitudinal axis "A" (FIGS. 1A-1B) of the bone screw construct 200 by resting atop fingers 24 of the coupling 20. A cutout 16 at the distal end of the housing 12 may facilitate placement of the housing 12 atop the bone screw construct 200. The plunger 10, shown in FIG. 4B, includes the indicator button 11 at the proximal end of the plunger and distal end 18 that includes contacting members 15. A cutout 19 at the distal end 18 of the plunger 10 may be included to inhibit the rod from interfering with determining the condition of the bone screw construct 200.

Figure 5A:
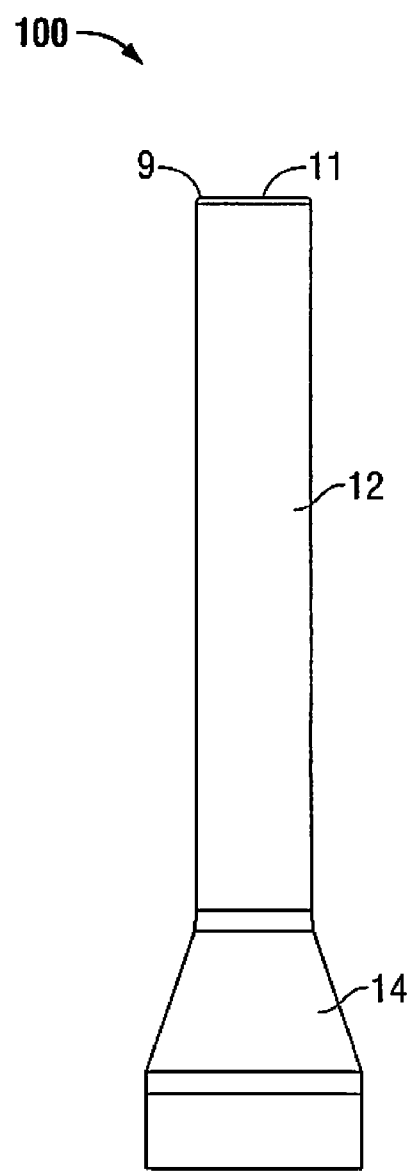
FIG. 5A is a front view of the lock indicator device of FIG. 4 shown in a first condition.
Figure 5B:
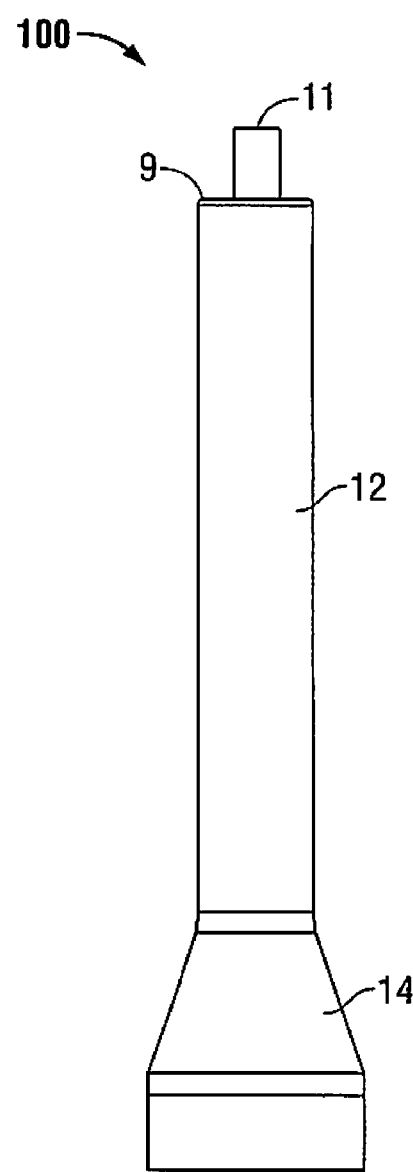
FIG. 5B is a front view of the lock indicator device of FIG. 4 shown in a second condition.
Figures 7, 7A:
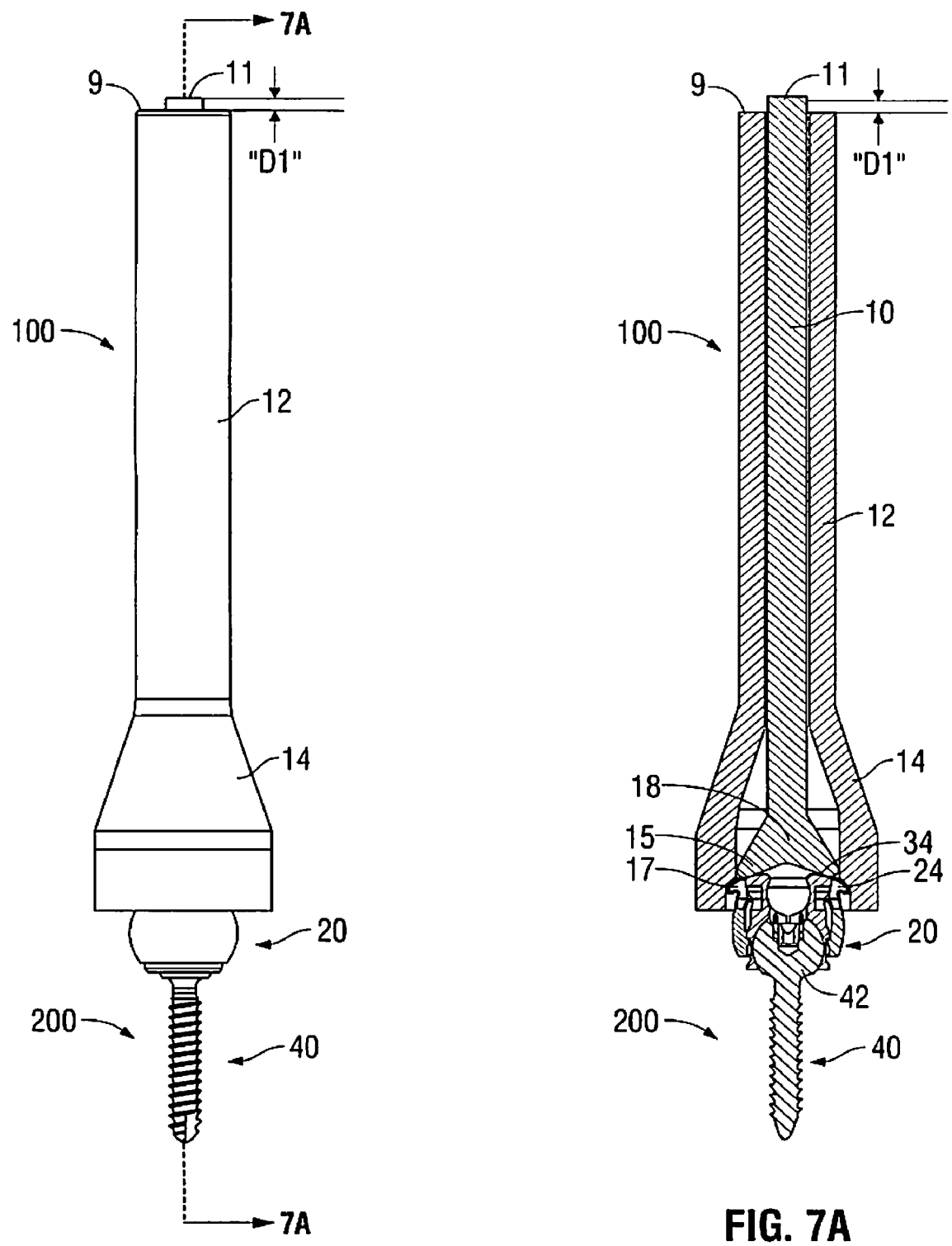
FIG. 7 is a front view of the lock indicator gauge of FIG. 4 coupled to the bone screw construct of FIG. 1A shown in a first condition.
FIG. 7A is cross-sectional view of the lock indicator gauge of FIG. 4 coupled to the bone screw construct of FIG. 1A as shown in FIG. 7A, taken along section line 7A-7A.
Figures 8, 8A:
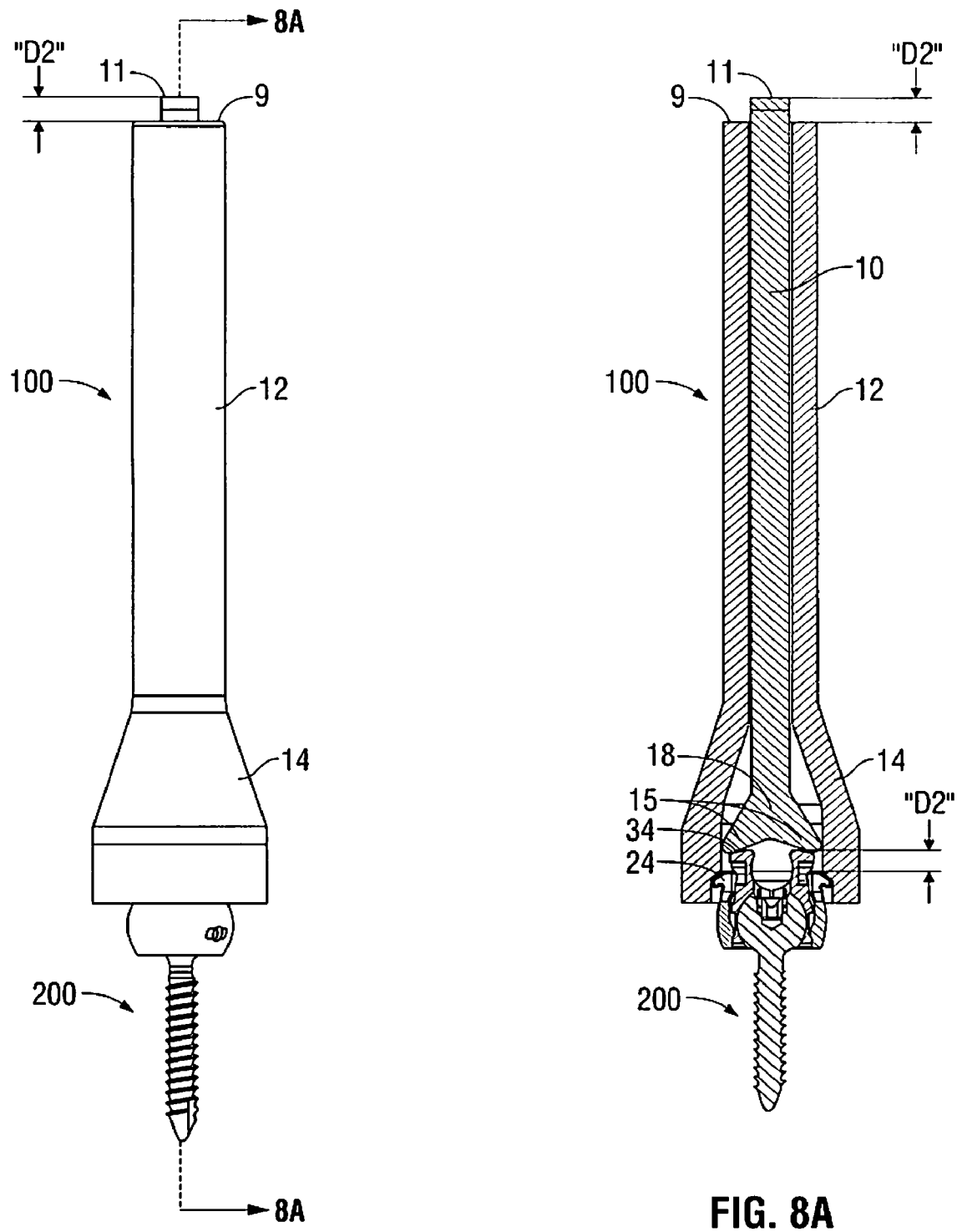
FIG. 8 is a front perspective view of the lock indicator gauge of FIG. 4 coupled to the bone screw construct of FIG. 1A shown in a second condition.
FIG. 8A is a cross-sectional view of the lock indicator gauge of FIG. 4 coupled to the bone screw construct of FIG. 1A, as shown in FIG. 8, taken along section line 8A-8A.

The indicator button 11 at the distal end of the plunger 10 has a retracted position (FIGS. 4, 5A, 7, 7A) and an actuated or extended position (FIGS. 5B, 8, 8A). The indicator button 11 may also be in an intermediate position between that of the actuated and extended positions to reflect a partially locked condition of the bone screw construct 200. Placement of the lock indicator gauge atop the bone screw construct 200 results in the indicator button 11 being in one of the actuated, the retracted, or the intermediate positions. An actuated position of the indicator button 11 corresponds to the unlocked state of the bone screw construct (FIG. 1B) such that a top surface of the indicator button 11 is spaced apart from top surface of the housing 12 by a distance "D2". Conversely, a retracted position of the indicator button 11 corresponds to the locked state of the bone screw construct (FIG. 1A). In the retracted position, the indicator button 11 may be substantially flush with a top surface 9 of housing 12, as shown in FIG. 4. Alternatively, a retracted position may be indicated when a top surface of the indicator button 11 is partially raised above top surface 9 of the housing 12 by distance "D1". The bone screw construct 200 may also be partially locked. In the event the bone screw construct 200 is partially locked, the plunger 10 will be displaced by a distance between that defined by distance "D1" and distance "D2".

A visual cue, e.g., a color or a mark, may indicate the position of the indicator button 11. Marks or visual cues (e.g., lines, grooves, words, lights, and/or colors) may be exposed or activated as the lock indicator gauge 100 is brought into contact with a bone screw construct 200. For example, visual cues may be longitudinally disposed along a length of the plunger 10 and may be exposed or activated as the indicator button 11 is extended from within housing 12. The visual cues or marks may be arranged in intervals to provide measurements as to the extent to which the plunger is extended from within housing 12. The visual cues or marks displayed is dependent upon the degree of displacement of the plunger 10, thereby providing indication of intermediate states in which the bone screw construct 200 may have between a fully locked state and a fully unlocked state, i.e., a partially locked state.

In an embodiment, the visual cues may be disposed at the proximal end of the plunger 10, e.g., a colored light such as a light emitting diode (LED) disposed at the proximal end of the lock indicator gauge 100. Furthermore, in embodiments of the present disclosure, the plunger 10 need not protrude from within housing 12 through a lumen 13 to provide an indication of the position of the plunger within the housing 12. For example, in another embodiment, the housing 12 may be partially or entirely transparent, thereby permitting visual inspection of the position of the plunger 10.

Figure 6:
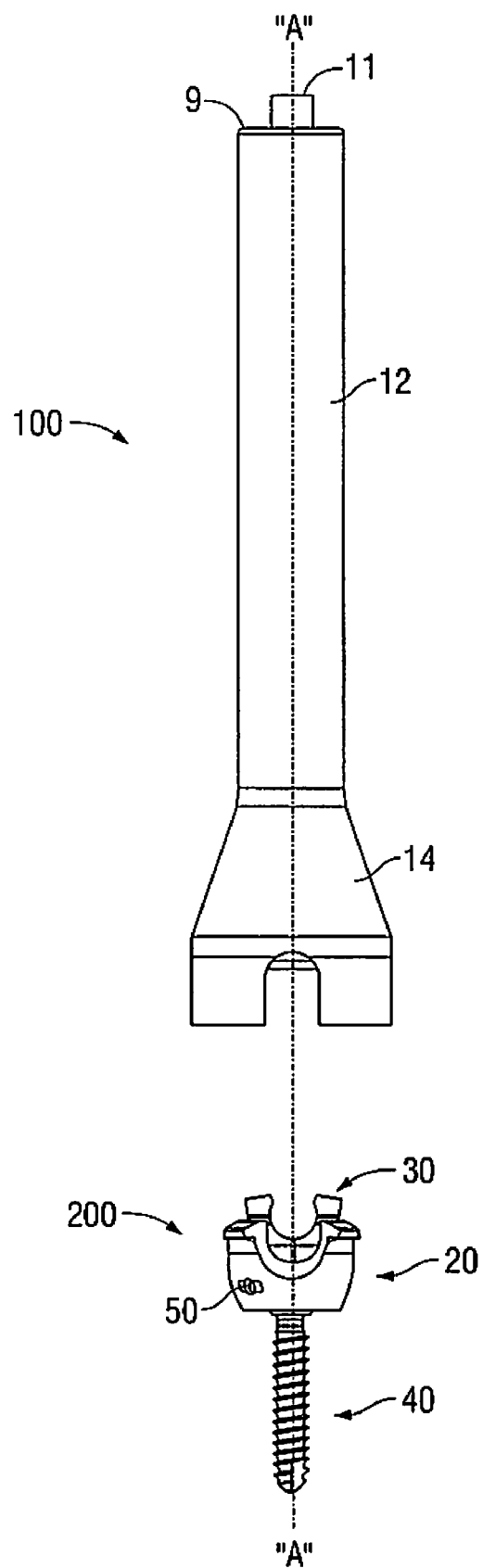
FIG. 6 is a front view of the lock indicator gauge of FIG. 4 shown relative to the bone screw construct of FIG. 1A.

Measurement of the relative distances between the collet 30 and the coupling 20 along axis "A" will now be described with reference to FIGS. 6-8A. As shown in FIG. 6, the lock indicator gauge 100 is brought into proximity with the bone screw construct 200, aligning the lock indicator gauge 100 and bone screw construct 200 along common axis "A". Placement of the lock indicator gauge 100 atop the bone screw construct 200 engages contacting members 17 of the receptacle 14 with the fingers 24 of the coupling 20. As the contacting members 17 rest atop fingers 24 of the coupling, the plunger 10 is urged proximally through lumen 13 as contacting members 15 of the plunger engage wings 34 of the collet 30. The plunger 10 is translated through the housing 12 by a distance defined between proximal surfaces 24a, 34a of the coupling 20 and collet 30, respectively.

A locked condition is indicated as shown in FIGS. 7 and 7A by the proximal translation of the plunger 10 and position of the top surface of the indicator button 11 above the top surface 9 of housing 12 by distance "D1". Conversely, an unlocked condition, is indicated as shown in FIGS. 8 and 8A, by the proximal translation of the plunger 10 and position of the top surface of the indicator button 11 above the top surface 9 of the housing by distance "D2".

In an embodiment, translation of the plunger 10 through the housing 12 of the lock indicator gauge 100 may result in an audible indication, e.g., a click. In other embodiments, translation of the plunger 10 through the housing 12 may result in a tactile indication, e.g., a user may feel a vibration.

Each of the embodiments described above are provided for illustrative purposes only. It will be understood that various modifications may be made to the embodiments of the present disclosure. Therefore, the above description should not be construed as limiting, but merely as exemplifications of embodiments. Those skilled in the art will envision other modifications within the scope and spirit of the present disclosure.

What is claimed is:

1. A lock indicator gauge system, comprising:
   a taper lock bone screw having a leading end, a trailing end, a collet, a coupling, and bone engaging shank, the collet and the coupling being supported on the bone engaging shank, the coupling being movable relative to the collet to position the taper lock bone screw between locked and unlocked states for securing a spinal rod to the collet and coupling; and
   a lock indicator gauge including:
      a housing having leading and trailing ends and including a receptacle supported on the leading end of the housing to receive the trailing end of the taper lock bone screw;
      a plunger being supported within a lumen defined between the leading and trailing ends of the housing, the plunger being movable relative to the housing between an extended position and a retracted position to correspond with one of the locked and unlocked states of the taper lock bone screw, the extended position being indicative of the unlocked state of the taper lock bone screw and the retracted position being indicative of the locked state of the taper lock bone screw.

2. The lock indicator gauge system of claim 1, wherein a trailing end of the plunger is spaced apart from the trailing end of the housing in the extended position and substantially flush with the trailing end of the housing in the retracted position.

3. The lock indicator gauge system of claim 1, wherein the plunger is positionable in an intermediate position between the extended and retracted position to indicate a partially locked state of the taper lock bone screw.

4. The lock indicator gauge system of claim 1, wherein a leading end of the plunger contacts at least one of the collet and coupling.

5. The lock indicator gauge system of claim 4, wherein the coupling is spaced from the leading end of the plunger when the plunger is disposed in the extended position and wherein the coupling is in contact with the leading end of the plunger when the plunger is disposed in the retracted position.

6. A lock indicator gauge for a taper lock bone screw, comprising:
   a housing including a proximal end, a distal end, and a first longitudinal axis, the housing including a lumen along the first longitudinal axis, a proximal end of a taper lock bone screw including inner and outer housings that are receivable within the distal end of the housing, the outer housing being movable relative to the inner housing for positioning the bone screw between locked and unlocked states to secure a spinal rod to the bone screw, the inner and outer housings each having a position along a second longitudinal axis, wherein the position of the inner housing may be the same or different from the position of the outer housing and wherein the first and second longitudinal axes are coaxial when the distal end of the housing receives the proximal end of the bone screw therein;
   a plunger longitudinally disposed within the lumen of the housing, the plunger being adapted to contact a portion of the bone screw and to translate relative to the housing along the first longitudinal axis by a distance corresponding to the positions of the inner and outer housings of the bone screw relative to one another along the second longitudinal axis; and an indicator to provide indication of a position of the plunger relative to the housing when the inner and outer housings of the bone screw are received within the distal end of the housing.

7. The lock indicator gauge of claim 6, wherein the indicator includes a proximal end of the plunger that extends through a lumen at the proximal end of the housing, the plunger extending through the lumen by a distance corresponding to the distance defined by the positions of the inner and outer housing relative to one another along the second longitudinal axis when the bone screw is received by the housing.

8. The lock indicator of claim 6, wherein the plunger includes at least one visual cue along a longitudinal surface.

9. The lock indicator gauge of claim 8, wherein the at least one visual cue is a mark, a groove, a color, or a word.

10. The lock indicator gauge of claim 6, wherein the position of the plunger may be visually inspected through the housing.

11. The lock indicator gauge of claim 6, wherein the indicator provides an audible indication.

12. The lock indicator gauge of claim 6, wherein the indicator provides a tactile indication.

* * * * *